US007390783B2

(12) United States Patent
Sparks

(10) Patent No.: US 7,390,783 B2
(45) Date of Patent: Jun. 24, 2008

(54) CHARGED PHOSPHOLIPID COMPOSITIONS AND METHODS FOR THEIR USE

(75) Inventor: Daniel L. Sparks, Aylmer (CA)

(73) Assignees: Ottawa Heart Institute Research Corporation, Ottawa, Ontario (CA); Liponex Inc., Ottawa, Ontario (CA)

( * ) Notice: Subject to any disclaimer, the term of this patent is extended or adjusted under 35 U.S.C. 154(b) by 311 days.

(21) Appl. No.: 10/956,065

(22) Filed: Oct. 4, 2004

(65) Prior Publication Data

US 2005/0080051 A1    Apr. 14, 2005

Related U.S. Application Data

(63) Continuation of application No. 10/148,391, filed as application No. PCT/CA01/01102 on Jul. 31, 2001, now Pat. No. 6,828,306.

(60) Provisional application No. 60/221,916, filed on Jul. 31, 2000.

(51) Int. Cl.
*A61K 38/00*    (2006.01)
(52) U.S. Cl. .......................................................... 514/2
(58) Field of Classification Search ........................ None
See application file for complete search history.

(56) References Cited

U.S. PATENT DOCUMENTS

| | | | |
|---|---|---|---|
| 4,466,958 A | | 8/1984 | Morrison |
| 4,492,659 A | | 1/1985 | Bosies et al. |
| 4,562,179 A | | 12/1985 | Teraji et al. |
| 5,128,318 A | | 7/1992 | Levine et al. |
| 5,231,090 A | | 7/1993 | Hsia et al. |
| 5,260,440 A | | 11/1993 | Hirai et al. |
| 5,573,779 A | | 11/1996 | Sato et al. |
| 5,614,507 A | | 3/1997 | Parker et al. |
| 5,746,223 A | * | 5/1998 | Williams .................... 128/898 |
| 5,948,756 A | * | 9/1999 | Barenholz et al. ............. 514/12 |
| 6,017,882 A | | 1/2000 | Nelsestuen |
| 6,079,416 A | | 6/2000 | Williams |
| 6,489,152 B1 | * | 12/2002 | Meyers ....................... 435/194 |
| 6,828,306 B2 | | 12/2004 | Sparks |
| 2002/0049183 A1 | * | 4/2002 | Yedgar et al. ................. 514/54 |

FOREIGN PATENT DOCUMENTS

| | | |
|---|---|---|
| DE | 19735776 | 2/1999 |
| GB | 1522664 | 8/1978 |
| JP | 04082833 | 7/1990 |
| JP | 08151334 | 11/1994 |
| JP | 9000206 A | 1/1997 |
| JP | 10017475 A | 1/1998 |
| WO | 8809345 | 5/1988 |
| WO | 8809345 | 12/1988 |
| WO | 9508986 | 4/1995 |
| WO | 9508986 | 9/1995 |
| WO | 9722333 | 12/1997 |
| WO | 9845463 | 2/1998 |
| WO | WO 01/12155 A1 | 2/2001 |
| WO | WO 01/82902 A1 | 11/2001 |

OTHER PUBLICATIONS

Burgess J.W. et al. "Phosphatidylinositol Increases HDL-C Levels in Humans." *Journal of Lipid Research* (2005) vol. 26: 350-355.
Cano-Cebrian, M.J. et al. "Intestinal Absorption Enhancement Via the Paracellular Route by Fatty Acids, Chitosans and Others: A Target for Drug Delivery." *Current Drug Delivery* (2005) vol. 2 No. 1: 9-22.
Maron, David J., et al. "Current Perspectives on Statins." *Circulation* (2000) vol. 101: 207-213.
Acton, Susan et al. (1996) "Identification of Scavenger Receptor SR-BI as a High Density Lipoprotein Receptor". *Science*. vol. 271: p. 518-520.
Allen, T.M., et al., "Liposomes with prolonged circulation times: factors affecting uptake by reticuloendothelial and other tissues.", *Biochemica et Biophysica Acta.*, Netherlands, May 19, 1989, vol. 981, No. 1, pp. 27-35, XP001075098.
Davidson, W. Sean. et al. (1994) "The Molecular Basis for the Difference in Charge Between Pre-β- and α-Migrating High Density Lipoproteins". *J. Biol. Chem.* vol. 269: p. 8959-8965.
Dobiasova, Milada. et al. (1991) "Cholesterol Esterification Rates in Very Low Density Lipoprotein—and Low Density Lipoprotein—Depleted Plasma". *Arterioscler. Thromb.* vol. 11 No. 1 p. 64-70.
Eisenberg, Shlomo. (1984) "High Density Lipoprotein Metabolism". *J. of Lipid Research.* vol. 25: p. 1017-1058.
Fielding, Christopher J. et al. (1995) "Molecular Physiology of Reverse Cholesterol Transport". *J. of Lipid Research.* vol. 36: p. 211-228.
Fountain, M.W., et al., "Enhanced intracellular killing of *Staphylococcus aureus* by canine monocytes treated with liposomes containing amikacin, gentamicin, kanamycin, and tobramycin.", *Current Microbiology,* (1981), 6/6, pp. 373-376, XP008010376.
Glomset, John A. (1968) "The Plasma Lecithin:Cholesterol Acyltransferase Reaction". *J. of Lipid Research.* vol. 9: p. 155-167.
Guérin, Maryse et al. (1993) "A New In Vitro Method for the Simultaneous Evaluation of Cholesterol Ester Exchange and Mass Transfer Between HDL and ApoB-Containing Lipoprotein Subspecies". *Arterioscler. Thromb.* vol. 14: p. 199-206.

(Continued)

*Primary Examiner*—Robert B. Mondesi

(57) ABSTRACT

The invention provides a pharmaceutical composition comprising a synthetic or naturally occurring charged phospholipid, which is formulated into a dosage form for administration to a subject or which is administered as a food additive. Negatively charged phospholipid composition increase the net negative charge on intravascular lipoproteins, enhance the clearance of cholesterol and regulate the function of lipolytic enzymes, retard prothrombin formation and aid in the clearance of virus and bacterial particles. Negatively charged lipid compositions can therefore be administered to humans and animals for the treatment of hyperlipidemia and blood coagulation disorders and to reduce the levels of virus, bacteria, and endotoxins in the blood stream. Positively charged lipid compositions can be administered to delay lipoprotein clearance from the plasma compartment and give longer duration of activity for drugs which are associated with lipoproteins.

19 Claims, 6 Drawing Sheets

OTHER PUBLICATIONS

Imaizumi K. et al. (1983) "The Contrasting Effect of Dietary Phosphatidylethanolamine and Phosphatidylcholine on Serum Lipoproteins and Liver Lipids in Rats". *J. Nutr.* vol. 113(12): 2403-11. PMID: 6686250.

J.E.F. Reynolds Ed., "Martindale—The Extra Pharmacopoeia", 1993, *The Pharmaceutical Press,* London, XP 002199383, pp. 1382, 1401, 1407.

Jonas, Ana. (1987) "Lecithin Cholesterol Acyltransferase". In *Plasma Lipoproteins* (A.M. Gotto Jr. ed.) Elsevier, Amsterdam. p. 299-333.

KAO Corp., Database WPI, Section Ch, Week 199711, Derwent Publications Ltd., London, GB; AN 1997-112796, XP002199384 & JP 09 000206 A, Jan. 7, 1997 (abstract).

Lagrost, Laurent. (1997) "The Role of Cholesteryl Ester Transfer Protein and Phospholipid Transfer Protein in the Remodeling of Plasma High-Density Lipoproteins". *Trends in Cardiovascular Medicine.* vol. 7(6): p. 218-224.

Markwell, Mary Ann K. et al. (1978) "A Modification of the Lowry Procedure to Simplify Protein Determination in Membrane and Lipoprotein Samples". *Analytical Biochemistry.* vol. 87: p. 206-210.

Miller, N. E. et al. (1977) "High-Density Lipoprotein and Coronary Heart-Disease: a Prospective Case-Control Study". *Lancet.* vol. 1: p. 965-967.

Murata, M. et al. (1982) "Effect of Dietary Phospholipids and their Constituent Bases on Serum Lipids and Apolipoproteins in Rats". *J. Nutr.* vol. 112(9): 1805-8. PMID: 7108644.

Okamoto, Hiroshi. et al. (2000) "A Cholesteryl Ester Transfer Protein Inhibitor Attenuates Atherosclerosis in Rabbits". *Nature.* vol. 406: p. 203-207.

Phillips, Michael C. et al. (1998) "Mechanisms of High Density Lipoprotein-Mediated Efflux of Cholesterol from Cell Plasma Membranes". *Atherosclerosis.* vol. 137: p. S13-S17.

Reynolds, J. E. F. (Editor) (1993) "Martindale—The Extra Pharmacopoeia". The Pharmaceutical Press, London. XP002199383.

Sagami Chem Res Centre, Database WPI, Section Ch, Week 199813, Derwent Publications Ltd., London, GB; AN 1998-140919, XP002199385 & JP 10 017475 A, anuary 20, 1998 (abstract).

Schaefer, Ernst J. et al. (1995) "Lipoproteins, Nutrition, Aging, and Atherosclerosis". *Am. J. Clin. Nutr.* vol. 61 (suppl): p. 726S-740S.

Schwartz, Charles C. et al. (1978) "Preferential Utilization of Free Cholesterol from High-Density Lipoproteins for Biliary Cholesterol Secretion in Man". *Science.* vol. 200: p. 62-64.

Sparks, Daniel L. et al. (1992) "Quantitative Measurement of Lipoprotein Surface Charge by Agarose Gel Electrophoresis". *J. Lipid Res.* vol. 33: p. 123-130.

Stuart, D.D., et al., "Pharmacokinetics of pegylated liposomal asODNs.", *Proceedings of the International Symposium on Controlled Release of Bioactive Materials,* (1998), $25^{th}$, pp. 366-367, XP008010375.

Tall, A. R. (1998) "An Overview of Reverse Cholesterol Transport". *European Heart Journal.* vol. 19 (Supplement A): p. A31-A35.

Wasan, K.M., et al., "Diversity of lipid-based polyene formulations and their behaviour in biological systems.", *European Journal of Clinical Microbiology & Infectious Diseases,* vol. 16, No. 1, 1997, pp. 81-92, XP008010351.

Wells, J.M., et al., "Electroporation-enhanced gene delivery in mammary tumors.", *Gene Therapy,* vol. 7, No. 7, Apr. 2000, pp. 541-547, XP008010350.

Zhao, Y., et al., "Effect of the apolipoprotein A-I and surface lipid composition of reconstituted discoidal HDL on cholesterol efflux from cultured fibroblasts.", *Biochemistry,* United States, Dec. 24, 1996, vol. 35, No. 51, pp. 16510-16518, XP001059130.

* cited by examiner

CHARGED PHOSPHOLIPID COMPOSITIONS AND METHODS FOR THEIR USE

CROSS-REFERENCE TO RELATED APPLICATIONS

This is a continuation of USSN 10/148,391 (now U.S. Pat. No. 6,828,306), which is based on International Application No. PCT/CA2001/001102, having an international filing date of Jul. 31, 2001, and which claims priority of U.S. Provisional Application Ser. No. 60/221,916, filed Jul. 31, 2000.

This invention relates to charged lipid compositions. In one aspect, this invention relates to negatively charged (anionic) lipid compositions, and the use of these lipid compositions for changing lipoprotein charge in vivo to clear cholesterol and other substances from the blood stream. In another aspect, this invention relates to positively charged (cationic) lipid compositions, and the use of these compositions to prolong drug activity.

BACKGROUND OF THE INVENTION

Atherosclerosis leading to coronary vascular disease is a primary cause of mortality in the developed world. Atherosclerotic risk has been shown to be directly related to elevated plasma cholesterol levels. In plasma about 70% of cholesterol is esterified to long-chain fatty acids to form cholesteryl esters and these cholesteryl esters are bound to plasma lipoproteins. The lipoproteins involved in the transport of cholesterol and cholesteryl esters include low density lipoprotein (LDL), high density lipoprotein (HDL), and very-low density lipoprotein (VLDL).

While high levels of cholesterol associated with LDL have been linked to atherosclerotic risk (Schaefer et al., 1995), high HDL cholesterol levels may be protective against the development of heart disease (Miller et al., 1977). As a result there has been significant effort to develop therapies which effectively reduce the level of LDL cholesterol and raise the level of HDL cholesterol within an animal. HDL may play an anti-atherogenic role by promoting the clearance of cholesterol from the body (Eisenberg, 1984). Furthermore, Schwartz et al. (1978) disclose that cholesterol in HDL is specifically targeted for excretion from the body by the liver in the form of bile. However, current therapies directed to reduce the level of LDL cholesterol and raise the level of HDL cholesterol have not met with success.

The factors that regulate cholesterol flux to the liver are poorly understood but may involve two distinct systems; a cellular sterol regulatory system and an intravascular transport system. Excess extrahepatic cholesterol may be transported in HDL particles to the liver for excretion (Glomset, 1968). HDL has also been shown to be able to adsorb cholesterol and cholesteryl esters (CE) from cell membranes (Phillips et al., 1998). In addition, a second sterol transport pathway may include transfer of cholesterol from HDL to the rapidly turning over VLDL lipoprotein pool, followed by clearance of cholesterol by the liver (Tall, 1998).

The mechanism of intravascular sterol transport is also poorly understood, but may involve the concerted action of multiple proteins and enzymes. Two enzymes thought be involved in intravascular sterol transport are lecithin:cholesterol acyltransferase (LCAT) and cholesterol ester transfer protein (CETP). At present it is thought that LCAT may form a concentration gradient to move sterol into and through the blood plasma compartment by promoting the conversion of free cholesterol (FC) to cholesterol esters (CE) on HDL particles (Jonas, 1987). CETP may then promote this lipid flux by moving the newly formed CE from HDL to an apoB containing lipoprotein pool (Lagrost, 1997).

All lipoprotein classes exhibit a net negative charge, due to both the apolipoprotein composition and its content of bound charged lipids (Davidson et al., 1994). However, individual bound lipids forming part of a lipoprotein can contribute either a net positive or a negative charge, or no charge at all, to the lipoprotein. Some phospholipids, when unbound, are negatively charged, some are positively charged, and some are electrically neutral. Examples of negatively charged phospholipids are phosphatidylinositol, phosphatidylserine, phosphatidylglycerol and phosphatidic acid. An example of an electrically neutral phospholipid is phosphatidylcholine. An example of a positively charged (cationic) phospholipid is dioleoyl trimethylammonium propane.

Williams U.S. Pat. No. 6,079,416 teaches administration of large liposomes containing phospholipids substantially free of sterols to treat hypercholesterolemia. Parker et al U.S. Pat. No. 5,614,507 teaches the injection of a bolus of phospholipid, with or without another electrically neutral lipid, to treat endotoxemia. However, the phospholipid compositions disclosed by Williams and Parker et al. are not electrically charged, so they would not act to change the electric charge of lipoproteins within the bloodstream. Instead, they act as a simple adsorbant to pick up and clear cholesterol or endotoxin from the blood.

U.S. Pat. No. 5,652,339 (Learch et al) and U.S. Pat. No. 5,128,318 (Levine et al) disclose the preparation of reconstituted high density lipoprotein (rHDL) particles, and suggest that rHDL particles may be used for drug administration and for treating diseases connected to lipids and lipodal substances. These rHDL particles said to be useable both in vivo or in vitro for removing lipid soluble materials (e.g. cholesterol, endotoxins) from cells or body fluids and aid in the treatment of hyperlipidemia and coronary atherosclerosis. Although, all lipoprotein classes exhibit a net negative charge as discussed above, these two patents teach nothing to increase the charge from that present in normal HDL.

Phosphatidylinositol (PI) is a negatively charged phospholipid found in all classes of lipoproteins and accounts for approximately 4% of the total phospholipid (PL) in HDL (Davidson et al., 1994). Incubation of PI with plasma or with isolated HDL, LDL or VLDL in vitro has shown that all of these lipoproteins can spontaneously absorb PI. However, little is known of what affects, or regulates, the amount of PI in different lipoprotein classes.

There is a need for novel compositions capable of enhancing hepatic clearance of lipoprotein particles thereby lowering cholesterol and tissue cholesterol, endotoxins and other lipid-soluble compounds such as some viruses and bacteria that associate with lipoprotein particles in vivo. There is also a need for methods to make use of such compositions. In particular, there is a need for such compositions, and methods for their use, which will preferentially lower the cholesterol associated with LDL. There is also a need for compositions, and methods for their use, which will retain drugs which associate with lipoproteins in the bloodstream, to increase the duration of the efficacy of such drugs.

SUMMARY OF THE INVENTION

The present invention provides negatively charged (anionic) lipid compositions that, when administered to an animal or subject, result in an increase in the in vivo lipoprotein negative electric charge. Associated with the increase in in vivo lipoprotein negative charge is an enhanced hepatic clearance of lipoprotein particles. The clearance of lipoprotein particles can be used for the clearance of cholesterol and has significant anti-atherogenic consequences. It can also be used to remove bacteria, endotoxin and viruses which associate with lipoproteins from the bloodstream, and for the treatment of lipid-associated diseases.

The invention also provides positively charged (cationic) lipid compositions which, when administered to an animal or subject, result in a decrease of the in vivo lipoprotein negative electric charge. Associated with the decrease in in vivo lipoprotein negative charge is a slowing of hepatic clearance of lipoprotein particles. This effect can be used to delay clearance of drugs which are associated with lipoproteins, thereby prolonging the efficacy of such drugs.

The present invention also comprises a pharmaceutical composition comprising a synthetic or naturally occurring negatively charged (anionic) phospholipid formulated into a dosage form for administration to a subject. If desired, the composition may comprise an admixture of two or more negatively charged phospholipids. The pharamaceutical composition is capable of mediating the level of lipid-associated compounds within an animal or subject. The invention also comprises the use of a negatively charged phospholipid composition as defined above for the production of a medicament useable to enhance clearance of cholesterol from the blood stream and cause the reduction in blood LDL and VLDL cholesterol levels.

The pharmaceutical compositions as discussed above can be provided in dosage forms comprising unilamellar vesicles multilamellar vesicles, multilamellar sheets, dispersions, micellar solutions, emulsions, microemulsions, pure lipid mixtures or any combination of these structures.

The present invention also relates to compositions as discussed above, wherein the dosage form is administered orally or as an injection intranasally or transdermally. In addition the composition may further comprise at least one pharmaceutically acceptable carrier.

The present invention also comprises an orally-administered food additive which comprises a charged phospholipid. When the charged phospholipid is a negatively charged phospholipid, the food additive is capable, when injected by a subject, of reducing the amount of cholesterol in the subject's bloodstream. A particularly preferred food additive comprises phosphatidylinosotol.

The present invention also relates to preferred compositions of those discussed above, wherein the charged phospholipid is a negatively charged phospholipid selected from phosphatidylinositol, phosphatidylserine, phosphatidylglycerol and/or phosphatidic acid or mixtures thereof, and particularly preferred compositions wherein the negatively charged phospholipid is phosphatidylinositol.

The invention also relates to a process for enhancing clearance of lipoprotein particles in vivo by administration of at least one negatively charged phospholipid. By increasing lipoprotein clearance, lipid-soluble compounds that associate with lipoprotein particles are also effectively removed. For example, as described herein, administration of charged phospholipid results in sterol mobilization into bile and excretion in faeces. Removal can therefore be accomplished of cholesterol, endotoxins, or lipoprotein-associated bacteria or virus particles. Without wishing to be bound by theory, it is thought that the administration of a pharmaceutical charged lipid composition to an animal or subject lowers serum levels of total cholesterol in the animal or subject, and inhibits the conversion of cholesterol to cholesteryl esters. Lipoprotein charge thus plays a role in regulating serum levels of lipoprotein-associated compounds, for example but not limited to free cholesterol and the like.

Also according to the invention, there is provided a method of lowering the level of cholesterol associated with LDL within a subject, the method comprising administering to the subject an effective amount of a composition comprising an anionic phospholipid composition.

Another aspect of the present invention pertains to the enhanced mobilization of cellular sterol, and the promotion of rapid clearance of both FC and CE from the plasma compartment, following the administration of a negatively charged phospholipid, (in a particularly preferred embodiment, PI) to a subject. Without wishing to be bound by theory, it is proposed that lipoprotein charge can affect cholesterol transport and that this process can be selectively manipulated by manipulating lipoprotein charge.

Other aspects of the invention provide methods of removing endotoxins, bacteria and virus particles, and treating lipid-associated diseases within an animal, including hyperlipidemia and atherosclerosis, by administering a negatively charged phospholipid to the animal or subject.

Another aspect of the invention provides a method for slowing the removal of lipoproteins, and drugs which associate with lipoproteins, from the bloodstream of an animal or subject by administering a positively charged phospholipid to such animal or subject. The invention also comprises compositions of positively charged phospholipids useful for such methods.

BRIEF DESCRIPTION OF THE DRAWINGS

These and other features of the invention will become more apparent from the following description in which reference is made to the appended drawings wherein.

DESCRIPTION OF PREFERRED EMBODIMENTS

Figure 1:
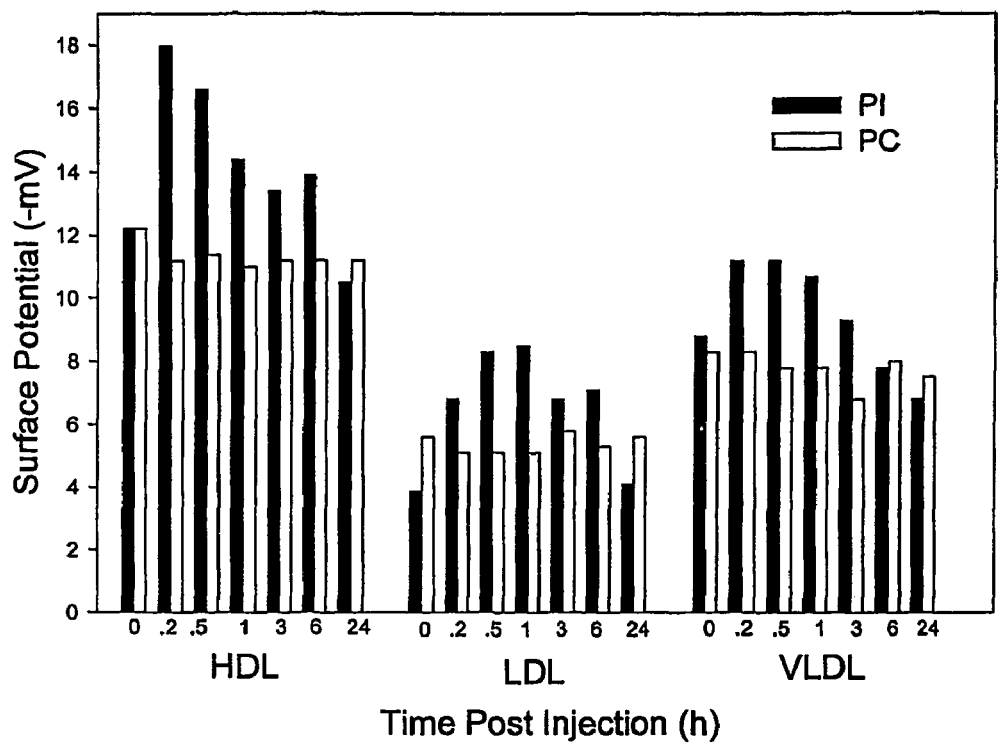
FIG. 1 depicts graphically the change in the negative surface charge of HDL, LDL and VLDL proteins following administration of phosphatidylinositol (PI) or phosphatidylcholine (PC) vesicles to rabbit.

Lipoprotein charge is affected by its content of charged molecules, predominantly charged lipids such as PI and non-esterified free fatty acids (NEFA). PI is an anionic lipid found in all classes of lipoproteins and accounts for approximately 4% of the total phospholipid in HDL (Davidson et al. 1994)

The present invention provides for a pharmaceutical composition comprising a charged phospholipid, either natural, analog, or a combination thereof, and in some cases, a suitable carrier. A suitable carrier may include, but is not limited to, phosphate buffered saline, sodium cholate, uncharged synthetic or natural ampliphatic lipid, HDL particles, or any protein capable of binding one or more charged phospholipids. The carrier can be one which permits delayed or timed release of the phospholipid, as is known in the carrier art.

The negatively charged (anionic) phospholipids of the invention include any negatively charged phospholipid that increases the negative charge of lipoprotein in vivo. Preferred negatively charged phospholipids of the present invention, are phosphatidylinositol (PI), phosphatidylserine (PS), phosphatidylglycerol (PG), phosphatidic acid (PA), or a mixture of any of these phospholipids. A particularly preferred phospholipid is phosphatidylinositol (PI).

The positively charged (cationic) phospholipids of the invention include any positively charged phospholipid that decreases the negative charge of lipoprotein in vivo. A preferred positively charged phospholipids is dioleoyl trimethylammonium propane (DOTAP).

The negatively charged phospholipid composition can be administered over a range of dosages that enhance clearance of cholesterol or other substances to be removed. When used in a pharmaceutical composition, administration in an amount from about 5 µM to about 100 µM per kg body weight of an animal or human subject is suitable. Preferably, the level of charged phospholipid administered to an animal or human subject is from about 5 µM to about 20 µM per kg body weight administered either in a single dose, or over a short period (eg. one hour). For example, which is not to be considered limiting, administration of PI in an amount from about 5 µM to about 100 µM per kg body weight of an animal or human subject enhances cholesterol mobilization as described herein.

When administration occurs by injection, the amount administered should preferably be enough to cause an increase in the negative surface potential on the surface of the HDL fraction of the blood of at least about 20% but preferably not more than 80% (ie. from a normal value of about −11 to −12.2 mV to a value of about −18 to −22 mV) for a transient period. Generally, the period lasts for at least one hour, and commences within a time of one minute to two hours after delivery to the body of the animal or human subject, although individual reactions may vary. The negative surface potential can. conveniently be measured by removal of blood samples from the animal or human subject, and observing the migration of the lipoproteins in an agarose gel, in the manner known in the art. It is found that oral administration causes a less marked change in charge of the HDL fraction than administration by injection, (for example, not to be considered limiting, from about −10.9 mV to about 12 mV), but that the transient period lasts longer with oral administration.

Susequent doses, or continuous administration at a low level for a suitable period of time, can be given to maintain the increased negative surface potential for a longer period than single dose administration would give.

In one embodiment, the charged phospholipid composition can be used for the production of a medicament. The medicament containing a negatively charged phospholipid can be used to enhance clearance of cholesterol, or to remove endotoxin or virus particles. The medicament containing the positively charged phospholipid can be used to slow lipoprotein clearance from the blood stream, and thereby slow removal from the bloodstream of a drug that associates with lipoproteins. The medicament can optionally also contain a drug that associates with lipoproteins, for example a drug associated with HDL or rHDL particles.

The medicament can be delivered by injection, or transdermally (as by a patch or a subcutaneous injection) or orally. The carrier is chosen, as known to one skilled in the art, to be compatible with the type of administration. For some types of administration, no carrier is necessary.

In another embodiment, the charged phospolipid composition can be included in a food. The food can then be administered to the subject, enhancing that subject's clearance of cholesterol. The phospholipid compositions can for example be dried and admixed into solid foods, or they can be mixed as an emulsion into liquid foods which will not neutralize them (for example, milk), or they can be sprayed onto solid foods (such as for example cereals) and allowed to dry before the foods are administered.

To demonstrate the role lipoprotein charge plays in cholesterol metabolism in vivo, intravenous injection of an uncharged phospholipid (phosphatidylcholine, PC) or a charged, anionic phospholipid {phosphatidylinositol, (PI) or phosphatidylserine (PS)}—into a fasted rabbit was examined. Similar effects occur with other test animals. PC injection has a negligible effect on lipoprotein charge and composition, similar to that observed in a saline injected animal. However, PI injection causes a significant increase in the net negative surface charge of all lipoproteins (see FIG. 1, discussed further below). This change in net negative surface charge is observed rapidly, for example, but not limited to after about 10 min, and is followed by a gradual return to regular levels by about 24 h, however, these time periods may vary depending upon the animal being treated. Alterations in the net charge of lipoproteins has also been observed when plasma is incubated in the presence of PI or PS. PI and PS show similar results.

In the studies conducted as described herein, no major changes in the levels of, or the composition of, HDL or LDL are evident over a 24 h turnover period. Co-injection of [$^3$H]-FC revealed an increase in the rate of clearance of labelled cholesterol from the PI injected rabbit plasma (see FIG. 5, discussed further below). In addition, the rate of cholesterol esterification by lecithin:cholesterol acyltransferase was almost completely inhibited in the PI animals (See FIG. 3, discussed further below.).

By the term "charged phospholipid" is meant a natural or synthetic glycerophospholipid which is electrically charged at neutral pH. A "negatively charged phospholipid" (also known as an "anionic phospholipid") has a negative charge at neutral pH. A "positively charged phospholipid" (also known as a "cationic phospholipid") has a positive charge at neutral pH.

Persons skilled in the art will understand that glycerophospholipids comprise a glycerol backbone wherein one of the hydroxyls is linked to a polar phosphate-containing group and the other two hydroxyls are linked to hydrophobic groups. Also evident to someone skilled in the art is that glyceride nomenclature is often defined in terms of a stereospecific numbering (sn) system, but that other stereochemical conventions such as D/L and R/S may be used, with most natural glycerophospholipids having the R or D configuration. The present invention contemplates charged phospholipids having either R or S (or equivalently D or L) configurations.

Most natural glycerophospholipids have hydrophobic groups attached to the sn-1 and sn-2 positions of the glycerol backbone, while a phosphate is usually attached at the sn-3 position. The hydrophobic groups usually comprise long chain hydrocarbons that are linked through ester or ether linkages. Thus, the present invention fully contemplates charged phospholipids comprising hydrophobic groups linked through ester or ether linkages. The hydrophobic groups may be any known in the art, for example but not wishing to be limiting, the hydrophobic groups may comprise saturated fatty acids such as lauric, myristic, palmitic, stearic, arachidic acid, or unsaturated fatty acids such as, but not limited to palmitoleic, oleic, linoleic, arachidonic acid, or any combination thereof.

The phosphate group of a glycerophospholipid is usually attached to the glycerol moiety at the sn-3 position and this phosphate group is linked to a head-group moiety. In phosphatidylinositol, the headgroup is inositol, while in phosphatidylserine, the headgroup is serine. The charged phospholipids of the present invention can have a phosphate group esterified to any hydroxyl of glycerol, with the remaining glyceryl hydroxyls esterified or attached via an ether bond to a hydrophobic group as defined above. In addition, the headgroup may optionally be substituted.

By the term "pharmaceutical composition" or "charged phospholipid composition" it is meant a composition comprising a charged phospholipid, as discussed above, that is formulated into an appropriate dosage form in the presence of a suitable carrier for administering to a subject. The carrier may consist of a buffer, for example but not limited to phosphate buffered saline, or a protein capable of associating with an charged phospholipid as described herein. For example, without limitation, the charged phospholipid can be formulated into structures such as unilamellar vesicles, multilamellar vesicles, multilamellar sheets, dispersions, micellar solutions, emulsions, microemulsions, or any combination thereof in the presence of phosphate buffered saline and the like as would be known to one of skill in the art, HDL particles, or any protein capable of associating with or binding charged phospholipid.

The formulations described above represent aqueous formulations. However, the charged phospholipid can be formulated as a solid, such as, without limitation, a powder that may form structures such as one or more of those discussed above when added to an aqueous solution. Also, the pharmaceutical composition may optionally include the addition of one or more pharmaceutically acceptable excipients as would be known to someone of skill in the art. For example, but not meaning to be limiting, the pharmaceutical composition may comprise other lipids to facilitate the formation of vesicular structures in solution. Alternatively pharmaceutical acceptable excipients such as but not limited to, hydrophilic phase components, lipophilic phase components and surfactants may be optionally included if the charged phospholipid is to be delivered in the form of an emulsion or microemulsion. Pharmaceutically acceptable excipients may also include, but are not limited to, solvents, buffers, antioxidants, and stabilizers as is known in the art.

The pharmaceutical composition of the present invention may be administered to a subject by any method known in the art. For example, and without limitation, the pharmaceutical composition can be administered orally or the pharmaceutical composition may be injected such as but not limited to intravenous injection, intramuscular injection, or intraperitoneal injection. However someone of skill in the art will understand that certain dosage forms may be more suitable to specific modes of administration. For example, if the pharmaceutical composition is to be administered intravenously as a vesicular solution, it is preferable for the charged phospholipid composition to be administered as unilamellar vesicles of cross-section sufficiently small so that they will not get caught in the microvasculature of a subject.

When the charged phospholipids of the present invention are administered as a food additive, they can be administered as part of any solid or liquid food with which they do not react or complex in such a way as to lose their charge. It is particularly preferred to administer the charged phospholipid or a mixture of charged phospholipids having the same charge in a dry state on or comminged in conventional cereal products, although other foods can also be used. In case of either a pharmaceutical or a food product, sufficient is administered to result in a change, for a period of at least 10 minutes, of the in vivo charge on the blood lipoproteins by at least 20%. The negatively charged phospholipids increase the negative charge of the lipoproteins, while the positively charged phospholipids decrease it.

The invention will be further illustrated in the following examples. However, it is to be understood that these examples are for illustrative purposes only, and should not be used to limit the scope of the present invention in any manner.

Procedures Used in Carrying Out the Examples a) Preparation of Phospholipid Vesicles 1-palmitoyl-2-oleoyl-phosphatidylcholine (PC) and 1-palmitoyl-2-oleoyl phosphatidylinositol (PI) vesicles are prepared by drying to completion 40 µmol of each lipid into a 12×75 mm culture tube under $N_2$. The lipids are solubilized in 3 mL of sterile saline comprising 150 mM sodium chloride (pH 7.2) by sonication for 1 minute at constant duty cycle. The vesicles are incubated at 37° C. for 10 minutes and then sonicated at a high output for 4 minutes in 10° C. water bath under $N_2$. In order to determine the rate of clearance of cholesterol from the test animals (rabbits), a radioactive tracer is added to the vesicle preparations prior to injection into the rabbit. 200 µL of 1 µCi/µmL [$^3$H]-FC is dried into a 12×75 mm culture tube with 40 µmol of PI or POPC. 3 ml of PBS is added to the dried lipids and the mixture is sonicated as described above. This tracer/vesicle preparation is injected and then 5 min later, the PI or PC vesicles were injected and blood is sampled as described below.

(b) Lipid Injection Into Rabbits

Male New Zealand white rabbits (3.5-4.0 kg) are fasted for 12 hours prior to injection and remain fasted until after data for the final time point is taken. Rabbits have free access to water during this time. A catheter is inserted into the marginal ear vein and blood samples are collected into tubes containing 7.5% ($K_3$) EDTA solution at the desired time points. A pre-injection blood sample is taken and the vesicle solution of either PI (n=4), or PC (n=2) or saline (n=1) is injected into the marginal ear vein. A sample of blood is removed at 10, 30 min, 1, 3, 6 and 24 h after the injection. All blood samples are placed on ice and then centrifuged at 3000 rpm for 15 min at 4° C. to separate the plasma. In order to ensure that lecithin:cholesterol acyl transferase (LCAT) is inhibited in the stored plasma, iodoacetamide (150 mM) is added to plasma samples as taught by Guerin et al. (1994).

Comparative studies are carried out in which the tracer is combined with 1 mg of PC and 3 mL of PBS instead of with PI and vesicles were prepared as described above. This is done to verify that PI is not affecting the incorporation/clearance of the tracer. The tracer incorporation and clearance was found not to be affected by the PI.

(c): Characterisation of Lipoproteins

Lipoprotein fractions are isolated by sequential ultracentrifugation (VLDL+IDL, d<1.019 g/mL; LDL, d=1.019-

1.063 g/mL; and HDL, d=1.063-1.21 g/mL) as known to one of skill in the art, and lipoprotein lipid composition (total cholesterol, free cholesterol (FC), and triglyceride (TG) concentrations) are determined enzymatically using kits from Roche Diagnostic (Laval, PQ). An aliquot of each lipoprotein isolated is dialysed into PBS and its surface charge characteristics were determined by electrophoresis on pre-cast 0.5% agarose gels using the procedure of Sparks and Phillips (1992).

(d): Measurement of Cholesterol Esterification

The effect of PI on LCAT activity is examined using plasma samples that are not treated with iodoacetamide. 400 µL aliquots of plasma for each time point are incubated for 30 min with 10 µCi of [$^3$H]-FC on filter paper discs (Dobiasova et al., 1991) at 37° C. and the reaction is terminated with the addition of 2 mL ethanol. Reaction products are extracted in hexane and the amount of [$^3$H] associated with CE and FC is determined by thin layer chromatography.

(e): Stimulation of Biliary FC Output and Sterol Excretion

Rabbits are injected with 40 µmol PI or PC vesicles containing 400 µCi [$^3$CH]-FC. Animals are sacrificed at 30 min, and bile is aspirated from the gall bladder. In addition the livers are harvested, homogenized and tissue radioactivity determined. Sterol excretion in the faeces is measured similarly except that faecal cholesterol levels are measured over a time period of 96 hours.

In Examples 1-8 and 11-12, the effect of a negatively charged phospholipid (PI or PS) is contrasted with the effect of a control. The control is an uncharged phospholipid (PC).

EXAMPLE 1

The Effects of Lipid Vesicles on Lipoprotein Surface Charge

Referring now to FIG. 1, there is illustrated the effect of injection of PI and PC vesicles on the estimated surface potential of HDL, LDL, and VLDL proteins in vivo. Injection of PC or saline (not shown) did not significantly affect migration of HDL, LDL and VLDL proteins into an agarose gel whereas injection of PI is associated with increased migration of all lipoprotein fractions into the gel. Without wishing to be bound by theory, the results indicate that the increased migration of the lipoprotein fractions following PI injection is attributable to an increased negative surface charge on the lipoproteins, possibly as a result of increased binding of the PI charged phospholipid species. PC, which is a neutral phospholipid, may also bind to the lipoproteins. However since PC is a neutral phospholipid, no significant change in the migration of the lipoproteins is observed. The increased migratory property of lipoproteins in a gel peaks following injection of PI and returns to normal by about 24 hours. This indicates that the increased negative surface charge imparted to HDL, LDL and VLDL lipoproteins is a result of charged phospholipid binding following PI injection, and that this negative surface charge is transient and reversible. Based on the migration patterns of the lipoproteins after removal from the subject in an agarose gel, it is estimated that the HDL fraction exhibits a background surface potential of about –12.2 mV, prior to the PI injection and reaches a peak negative charge of about –18.0 mV about 10 minutes after PI injection. Similarly, the VLDL fraction is estimated to have an initial surface potential of about –8.8 mV, which increases to about –11.2 mV after 10 minutes. LDL is estimated to have an initial surface potential of about –3.9 mV, and peaks about 60 min after the PI injection at about –8.0 mV.

This change in surface charge in the phospholipid compositions as described herein, alters the metabolism of lipids and lipid-soluble compounds, for example cholesterol, in such a manner that these lipid-soluble compounds are lowered in a subject as described for cholesterol, below.

EXAMPLE 2

The Effects of Negatively Charged Phospholipid on Lipid Transfer in Plasma

Figure 2:
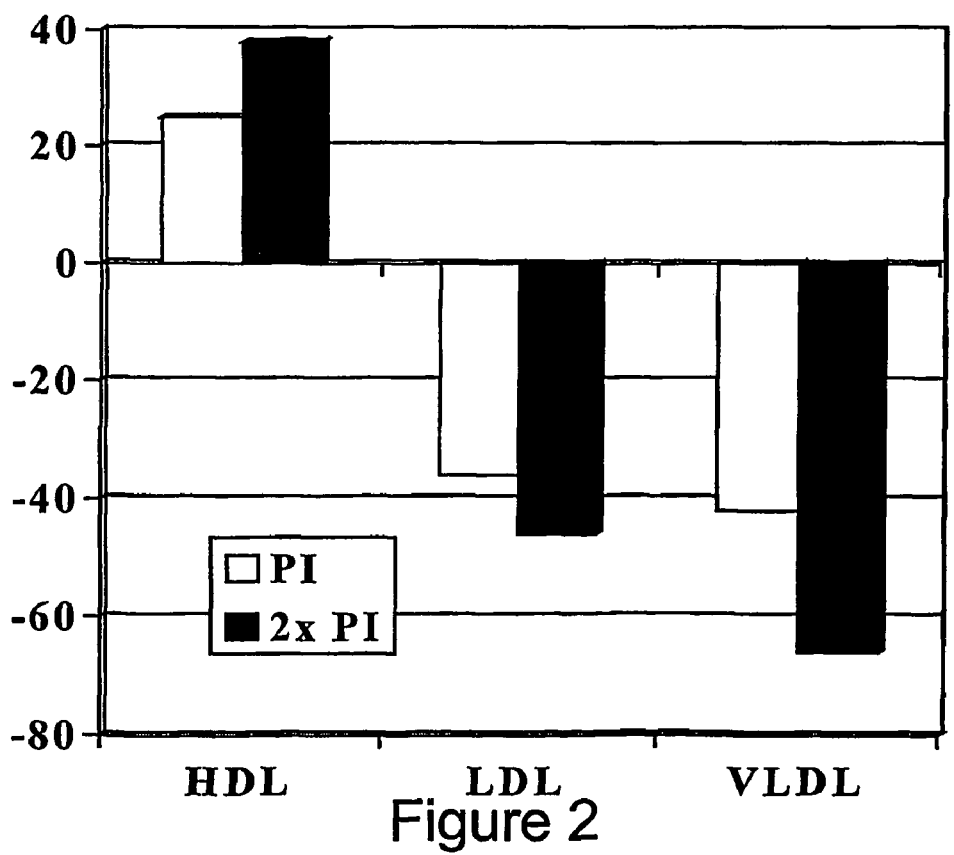
FIG. 2 shows a graphical representation of the effect of PI on lipoprotein cholesterol levels in plasma from a fasted normolipidemic subject

Referring now to FIG. 2, there is graphically depicted the effect of incubations with PI on the amount of cholesterol associated with HDL (high density lipoprotein), LDL (low density lipoprotein) and VLDL (very low density lipoproteins) following isolation of lipoproteins from plasma of fasted normolipidemic subjects. The addition of PI to blood plasma of a subject is found to be associated with a reduction of cholesterol in LDL and VLDL and increase in HDL cholesterol levels. Without wishing to be bound by theory, the results indicate that PI stimulates the transfer of CE and FC from LDL and VLDL to HDL. This appears due to the electrostatic effects, that increased lipoprotein PI concentrations have on cholesteryl ester transfer protein. Previous work has shown that this protein controls interlipoprotein cholesterol transfers and is affected by lipoprotein charge (Lagrost 1997).

EXAMPLE 3

Inhibition of Cholesterol Esterification by Negatively Charged Phospholipid

Figure 3:
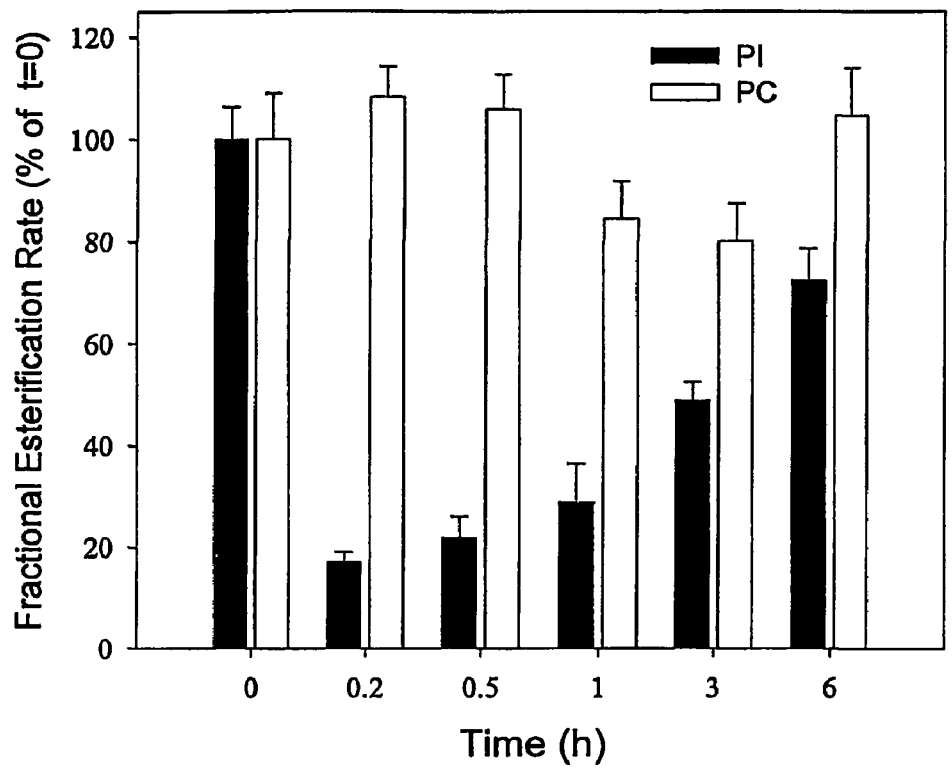
FIG. 3 shows the effect of injection of PC or PI into rabbits on plasma cholesterol esterification.

Referring now to FIG. 3, the graph shows the effect of PC or PI injection within an animal on the rate of cholesterol esterification by LCAT at various times following injection of PI or PC in vivo. No appreciable change in LCAT activity is observed after injection of PC vesicles. However, endogenous LCAT activity is reduced to about 18% that of normal (PC injected control) after about 10 min post injection of PI. Also, PI injection reduces the fractional rate of cholesterol esterification from about 45% to about 8%, of initial values, per hour. After a period of time following PI vesicle injection, as shown in FIG. 3, LCAT activity returns to about 75% of normal. Without wishing to be bound by theory, these results indicate that PI may inhibit CE production by lecithin:cholesterol acyl transferase (LCAT).

To investigate the effect of PI on the production and transport of CE in the plasma, the amount of radioactive CE was measured at each time point (data not shown). The levels of [$^3$H]-CE in the PI and PC injected rabbits were significantly different. Most notably, at the initial time points, there was 85% less [3H]-CE in the PI injected rabbit, than in the control. This indicated that the production of CE may be impaired in the PI rabbits, and therefore the endogenous activity of LCAT in plasma was measured (FIG. 3). The data shows that enrichment of plasma lipoproteins with PI almost completely inhibits cholesteryl esterification by LCAT. Without wishing to be bound by theory, the results indicate that the reduced levels of [$^3$H]-CE in PI injected animals were primarily due to a decreased production by LCAT. Since plasma CE levels actually rise in the presence of PI (and LCAT inhibition), the data indicate that LCAT is not solely responsible for the amount of CE in plasma lipoproteins. Rather it appears that PI may modify intravascular cholesterol levels by mobilizing a cellular cholesterol pool.

EXAMPLE 4

Figure 4:
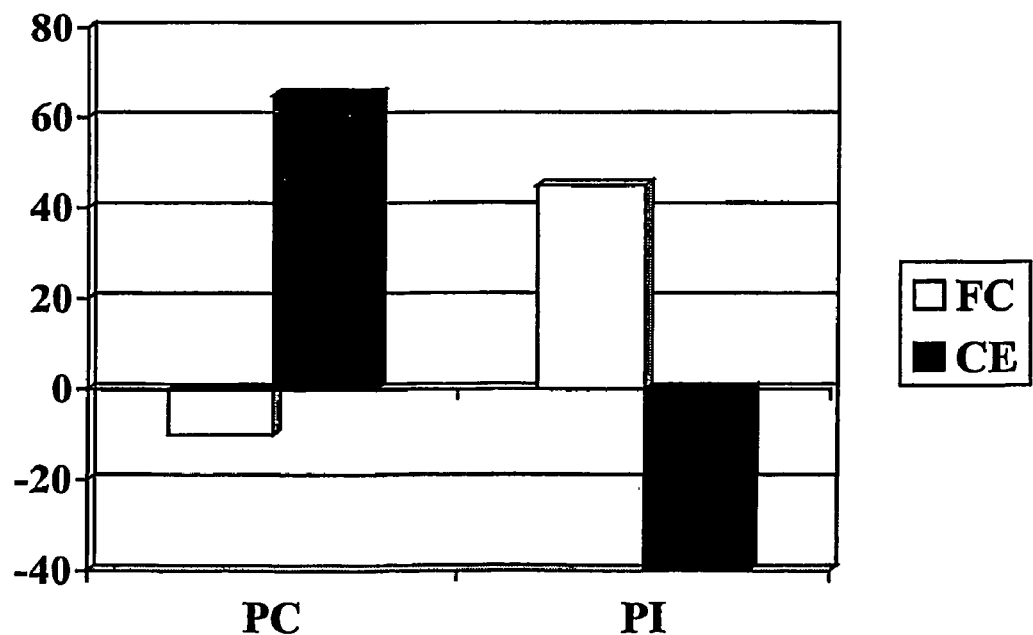
FIG. 4 shows the effect of incubations with PC or PI on the lipoprotein levels of FC and CE in human blood.

Effect of Negatively Charged Phospholipids on Lipoprotein—Red Blood Cell Interactions Referring now to FIG. 4, there is graphically depicted the effect of PI or PC vesicles on lipoprotein CE and FC. Incubation of whole blood with PC vesicles results in a 60% increase in the CE content of the lipoproteins, while FC content is reduced by about 10%. In contrast, PI vesicle incubation with whole blood indicates that lipoprotein CE is reduced by about 40% while FC levels increase by about 40%. Negatively charged phospholipids appeared to promote a reciprocal exchange of CE for FC between red blood cells and the lipoprotein particles. However, since CE did not accumulate in the red blood cells, the experiment shows that PI stimulates a red blood cell associated CE hydrolase that can hydrolyse lipoprotein CE. It has previously been taught that red blood cells cannot store CE and therefore utilize a membrane-bound CE hydrolase to maintain membrane FC levels. Without wishing to be bound by theory, the results therefore indicate that PI stimulates the degradation of lipoprotein CE.

EXAMPLE 5

Effect of PI on the clearance of [$^3$H]-FC from the Blood of a Rabbit

Figure 5:
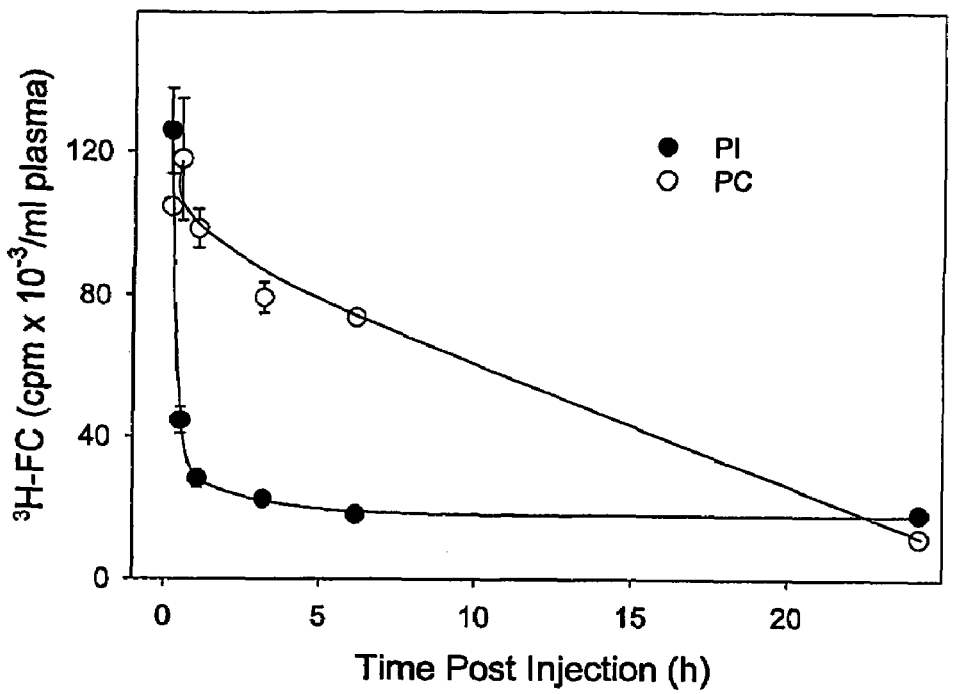
FIG. 5 shows the time clearance of [$^3$H]-FC from the blood stream of a rabbit following administration of Pi and PC vesicles containing [$^3$H]-FC.

Referring now to FIG. 5, there is shown the clearance of [$^3$H]-FC at various times after rabbits are injected with [$^3$H]-FC and either PI or PC vesicles. FIG. 5 shows that [$^3$H]-FC in plasma of PI injected rabbits falls to about 15% of the initial dose after about 1 h. In comparison, rabbits injected with PC contain approximately 90% of the injected radioactivity after 1 h. Further, the PC injected rabbit requires longer than about 6 h to clear the [$^3$H]-FC to a comparable baseline level, when compared with an animal injected with PI, under identical conditions. The half-life of [$^3$H]-FC in the PI injected rabbits is determined to be about 0.3 h and is about 30-fold shorter than that for the PC injected rabbits (about 8.4 h).

To verify that [$^3$H]-FC was not affected by co-injection of [$^3$H]-FC with different lipids, [$^3$H]-FC was combined with a small amount of PC, injected into a rabbit and then PI vesicles were injected 5 min later. These experiments showed a similar rapid clearance of [$^3$H]-FC as was seen with the co-injection of PI and [$^3$H]-FC.

EXAMPLE 6

Effect of Negatively Charged Phospholipid on Biliary FC Output

Figure 6:
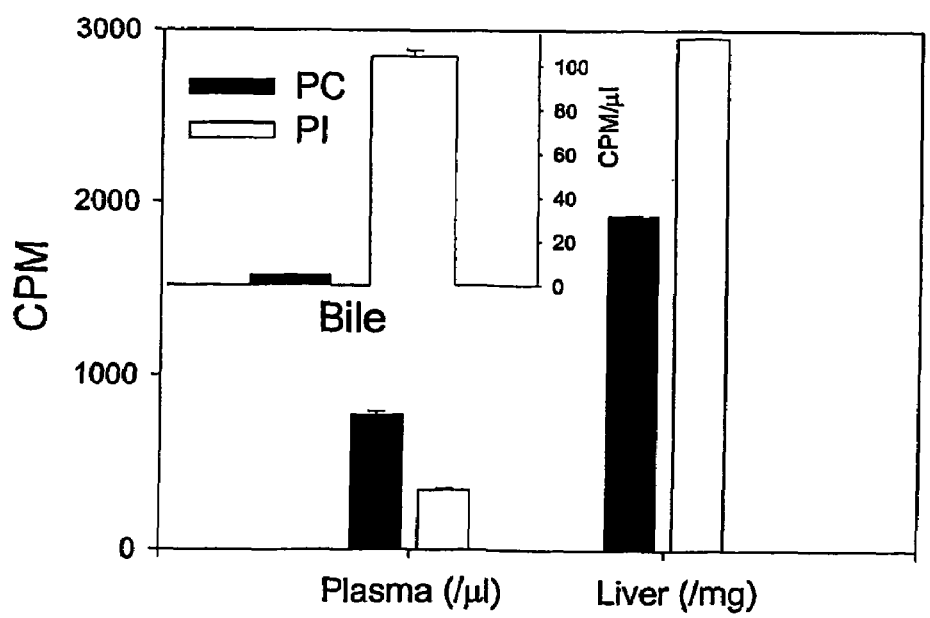
FIG. 6 shows the effect of PI on biliary FC output. Rabbits were injected with PI or PC vesicles containing [$^3$H]-FC and then sacrificed at 30 min.

Referring now to FIG. 6, there is shown the effect of PI on biliary FC output after rabbits are injected with PI or PC vesicles containing [$^3$H]-FC. In comparison to PC, PI injection is associated with a reduction of [$^3$H]-FC in plasma, and an elevation of [$^3$H]-FC in the liver. Without wishing to be bound by theory, PI may enhance the clearance of cholesterol from plasma and promote its uptake and accumulation in the liver. In addition, PI injection appears to be associated with an increase output of cholesterol into bile. About 20-fold enhanced output of cholesterol into bile is observed (FIG. 6). These results suggest that PI is capable of lowering plasma cholesterol levels by stimulating hepatic uptake and excretion of free cholesterol in bile.

EXAMPLE 7

Effect of Negatively Charged Phospholipid on Sterol Excretion

Figure 7:
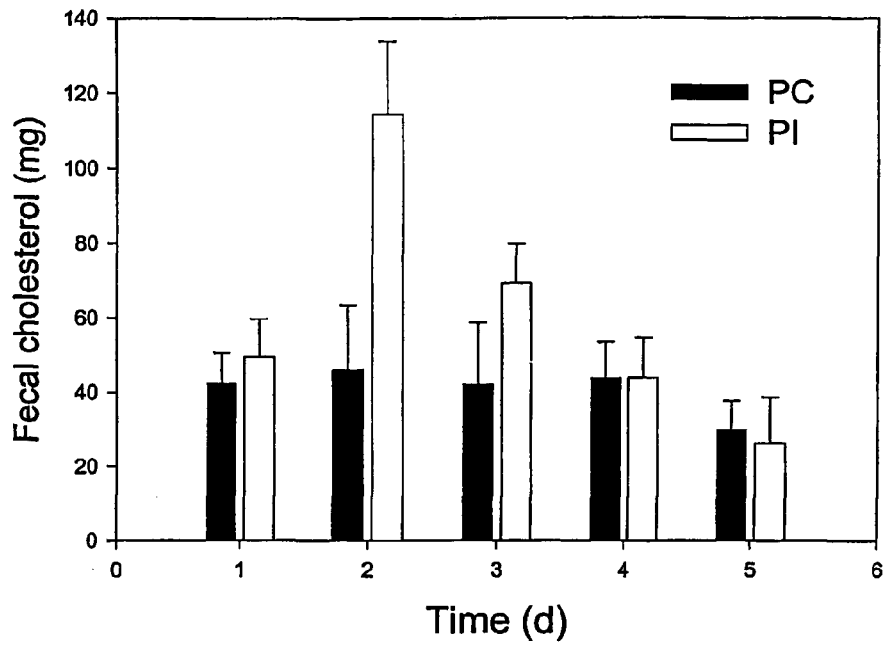
FIG. 7 shows the effect of PI or PC injections into rabbits on faecal cholesterol excretion.

Referring now to FIG. 7, there is graphically depicted the effect of PI injection associated with sterol excretion. FIG. 7 suggests that PI injection enhances faecal cholesterol output. PC injection into a rabbit had no effect on cholesterol excretion, while PI injection enhanced faecal cholesterol output by about 300% at 2 days post injection. The increase in cholesterol output returned to normal by about day 4. These results show that PI can stimulate sterol excretion.

EXAMPLE 8

Figure 8:
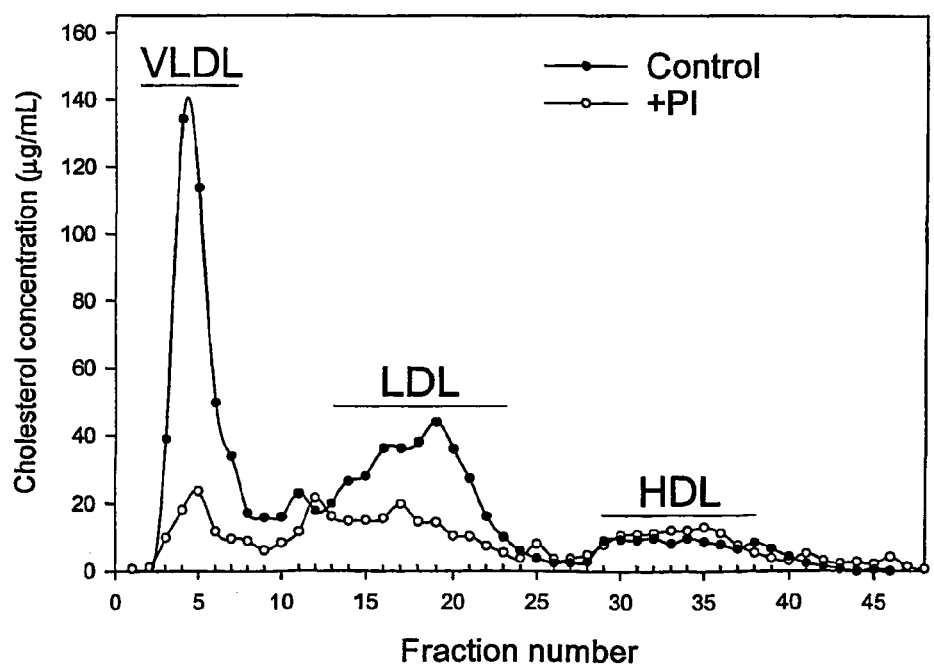
FIG. 8 shows the effect of Pi injections into hypercholesterolemic rabbits on HDL, LDL and VLDL cholesterol levels.

Effect of Negatively Charged Phospholipids on the Treatment of Hypercholesterolemia Referring now to FIG. 8, there is graphically depicted the effect of PI injection on lipoprotein cholesterol levels in hypercholesterolemic rabbits. Rabbits were fed a diet enriched in cholesterol for a period of 4 weeks to increase the levels of cholesterol in the LDL and VLDL particles in the bloodstream. One half of the study rabbits were then injected with 36 mg of PI 2× daily for 7 days. On day 7, plasma samples were drawn and lipoproteins were fractionated by size exclusion chromatography on two Superose 6 columns. Shown are gel filtration profiles for the different rabbit plasmas, which illustrate the levels of cholesterol in the various lipoprotein fractions. The untreated hypercholesterolemic rabbit plasma sample is shown to have high levels of LDL and VLDL cholesterol. PI injections caused a greater than 7-fold reduction in VLDL cholesterol and about a 2.5-fold reduction in LDL cholesterol levels over the 7 day period. In contrast, PI slightly increased the amount of cholesterol in the HDL particles. PI therefore can be used to treat hypercholesterolemia and reduce plasma LDL and VLDL cholesterol levels.

EXAMPLE 9

Figure 9:
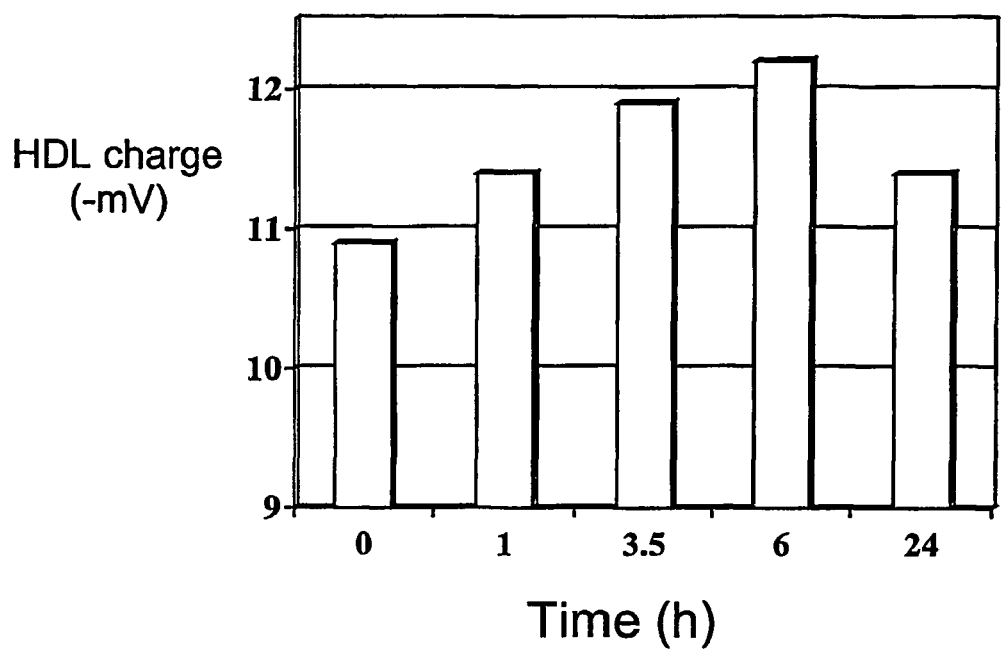
FIG. 9 shows the effect of the oral administration of PS on HDL charge in a human subject.

Effect of Orally Administered Negatively Charged Lipids on Lipoprotein Charge Referring now to FIG. 9, there is graphically depicted the results of oral administration of 300 mg of PS to a human subject. Plasma samples were drawn before, and over a 24 hour period after, administration of PS. HDL charge was determined electrokinetically after electrophoresis of the plasma samples on 0.5% agarose. HDL charge progressively increased from −10.9 mV to over −12 mV by 6 hours, and then fell to −11.4 mV by 24 hours post injection. Similar results have been observed when PI was dried onto rabbit chow and then fed to rabbits (data not shown). Thus, orally administered negatively charged lipids is absorbed intestinally and alters lipoprotein charge in the blood stream.

EXAMPLE 10

Effect of Lipoprotein Charge on Lipoprotein Lipase and Hepatic Lipase

Figure 10:
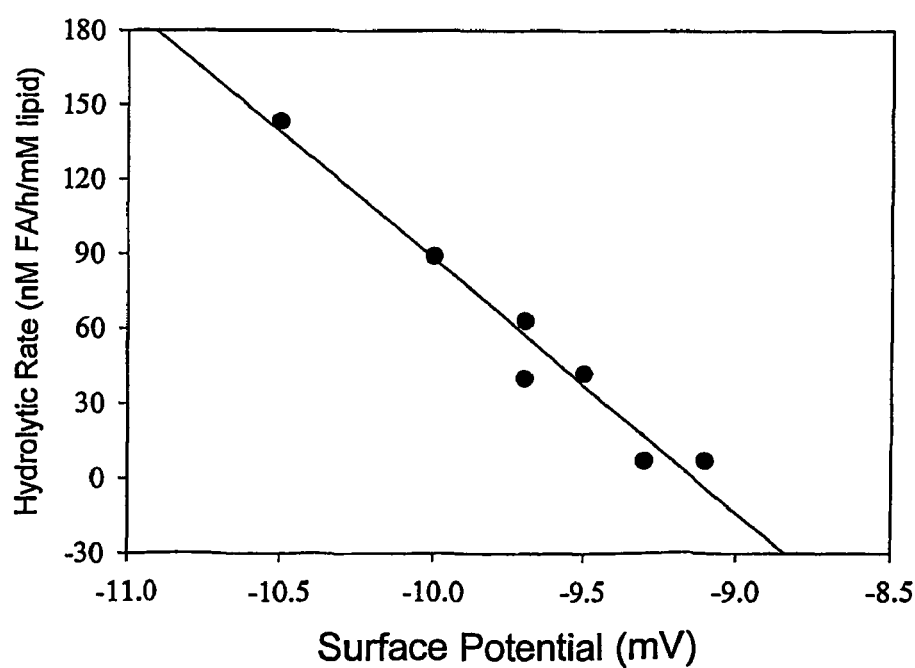
FIG. 10 shows the effect of lipoprotein charge on lipolysis by hepatic triglyceride lipase.

Referring now to FIG. 10, there is shown the effect of lipoprotein charge on hepatic lipase. High density lipoprotein particles were enriched to contain various amounts of anionic or cationic lipids and then characterized as substrates for pure human hepatic lipase. Decreasing the net negative charge on the lipoprotein was associated with a reduction in the lipolytic activity of is hepatic lipase. Lipoprotein charge can also be used to regulate lipoprotein lipase. Enriching plasma with PI was shown to stimulate lipid hydrolysis by lipoprotein lipase, while addition of the cationic lipid, DOTAP, had the opposite effect and inhibited lipid hydrolysis (not shown). Lipid hydrolysis by hepatic or lipoprotein lipase can therefore be affected by alterations in the charge properties of plasma lipoproteins.

EXAMPLE 11

Effect of Charged Lipids on Plasma Clotting Time

Figure 11:
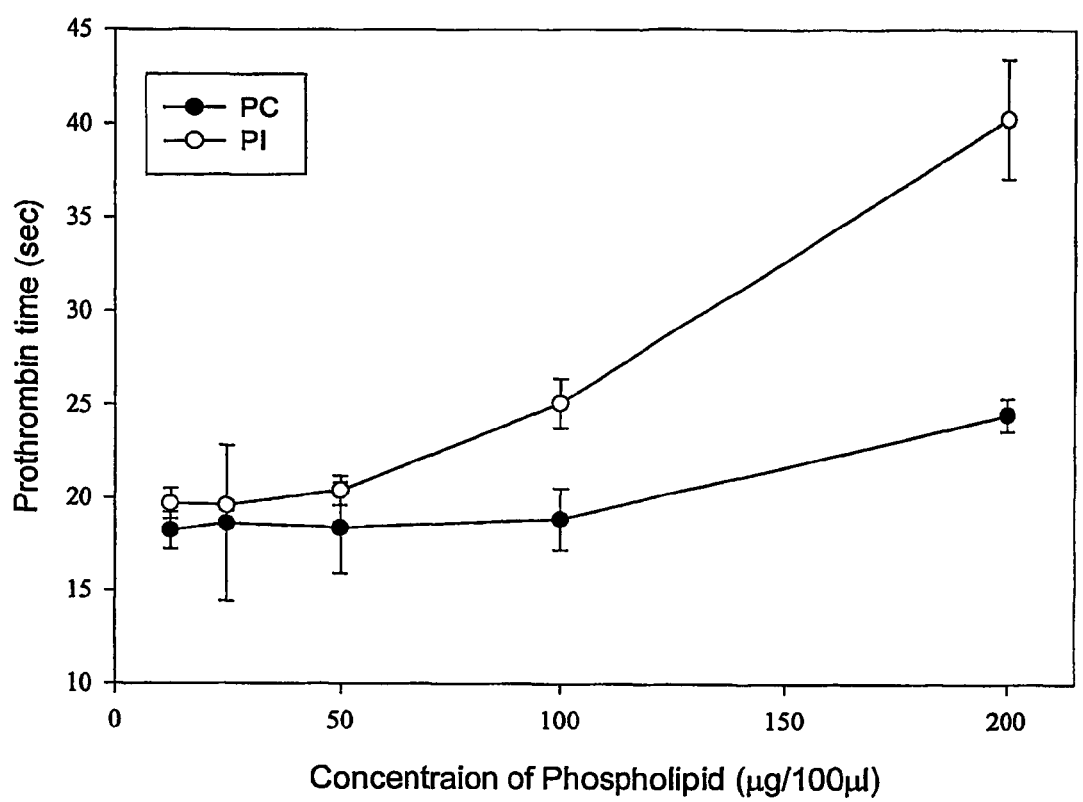
FIG. 11 shows the effect of charged lipids on plasma clotting time.

Referring now to FIG. 11, there is shown the effect of charged lipid on blood coagulation. Human plasma was incubated with various amounts of uncharged vesicles, phosphatidylcholine (PC) or anionic vesicles, phosphatidylinositol (PI), for 24 h at 4° C. Prothrombin time was then measured with the use of a commercially available kit. The results are shown in FIG. 11. Increasing amounts of PC has no significant effect on plasma clotting time, while PI caused an inhibition to the formation of prothrombin.

EXAMPLE 12

Effect of Charged Lipid on the Clearance of Cytomegalovirus from the Plasma of a Rabbit Rabbits were injected with $8 \times 10^{10}$ cytomegalovirus (CMV) particles and then with 36 mg of either uncharged vesicles, phosphatidylcholine (PC), or anionic vesicles, phosphatidylinositol (PI). Blood samples were taken at specific intervals and the amount of virus in the blood samples was determined by immunometric analysis. The results were demonstrated in a CMV p28 western blot of a blood sample taken at 10 minutes post injection (not reproduced in this document). PI caused a 1.7-fold increased rate of clearance of the CMV injectate relative to that observed with PC.

EXAMPLE 13

Effect of Anionic and Cationic Lipids on Lipoprotein Charge in Human Plasma

Different concentrations as shown below of negatively charged phospholipid (PI) or positively charged phospholipid (DOTAP) were added to human plasma and the surface charge on the lipoproteins was determined. The human plasma was incubated with PI or dioleoyl trimethylammonium-propane (DOTAP) vesicles for 24 h at 4° C. and then electrophoresed on 0.5% agarose. Lipoprotein charge was calculated from electrokinetic analyses. Results were as follows:

| Lipid Added | concentration (mg/ml) | Lipoprotein Surface Charge (-mV) | | |
|---|---|---|---|---|
| | | VLDL | LDL | HDL |
| None | 0 | 5.5 | 2.5 | 11.8 |
| PI | 5 | 6.3 | 2.9 | 12.4 |
| | 10 | 6.8 | 3.3 | 12.8 |
| | 50 | 6.9 | 3.4 | 13.2 |
| | 100 | 7.1 | 3.6 | 13.4 |
| DOTAP | 5 | 4.6 | 2.2 | 11.4 |
| | 10 | 4.6 | 1.9 | 11.2 |
| | 50 | 4.1 | 1.9 | 11.0 |
| | 100 | 4.1 | 1.7 | 10.9 |

Discussion of the Examples

Aspects of the present invention have been described in Examples 1-2 using both rabbits and humans as experimental models. However, similar results are expected to occur in other animals. Therefore, the present invention contemplates using pharmaceutical compositions comprising negatively charged phospholipids to lower the level of cholesterol to treat lipid associated diseases, and to clear endotoxins, bacteria, viruses in any animal or human subject. An animal may include, but is not limited to, monkey, dog, cat, pig, etc. A "subject", as the term is used herein, is a human or animal subject, unless the context shows otherwise. The animal results are thought to predict accurately the effect on a human subject, particularly as the animals used in the animal studies gave similar results to the human studies in the examples containing human studies, and because the animals chosen are conventionally used for studies of lipoproteins, cholesterol and the like because of the similarity of their reactions to those of humans.

Further, although the examples use PI and PS as a representative examples of a negatively charged phospholipid that is capable of mediating the surface charge of the phospholipid composition, and reducing the level of a lipid-soluble compounds in an animal or subject, it is found that other negatively charged phospholipids also display similar properties to those described f. Thus, the present invention contemplates the preparation and use of other negatively charged phospholipids in addition to PI, for example but not limited to PS, PG, and PA, within pharmacological compositions that are capable of regulating the hepatic clearance of lipoprotein-associated compounds in an animal or subject, or as a food additive.

Injection of PI vesicles into a rabbit caused a dramatic increase in negative surface potential of all classes of lipoprotein (FIG. 1). This appears to be directly due to the incorporation of the charged lipid into the lipoproteins. Incubation of PI with plasma or with ultracentrifugally isolated HDL, LDL or VLDL in vitro indicates that all lipoproteins can spontaneously adsorb PI in a manner that appears phospholipid transfer protein (PLTP) independent, as ultracentrifuged lipoproteins are devoid of this protein.

PI mass measurements show that most of the PI is associated with the HDL particles and the level of PI increases rapidly, from initially being below detection levels, to up to 30% of the total HDL-PL, after 10 min. After this time, the HDL-PI content slowly decreased to about 5-10% of the HDL-PL by 3 h. The clearance of PI from the different lipoproteins may have been due to either a lipoprotein-cellular transfer or to a selective hydrolysis by a charged phospholipid specific phospholipase.

When the clearance of [$^3$H]-FC from plasma is monitored, the data show that after the injection of PI, the tracer is much more rapidly cleared from the plasma, than compared to the rabbit injected with the equivalent amount of PC (FIG. 5). This clearance is not the result of an increased conversion of FC to CE, as very little [$^3$H]-CE is detectable, and LCAT is almost completely inhibited at the early time points. Therefore, these results show that PI stimulates a rapid flux and clearance of cholesterol from the plasma compartment. Several lines of evidence suggest that this clearance of FC may involve an increased hepatic uptake of this lipid. Without limitation as to theory, therefore, it is thought that PI may directly enhance interactions with the HDL receptor, SR-BI, within caveolin enriched domains, and promote a selective clearance of both FC and CE through this receptor.

These examples show that injection of a charged phospholipid, can dramatically affect cholesterol transport in vivo. The data indicates that changes induced in lipoprotein cholesterol metabolism by negatively-charged phospholipids are a result of altered interactions between the charged phospholipid-enriched lipoproteins and specific cell surface microdomains, as well as a change in interactions with the plasma proteins involved in lipoprotein remodelling and metabolism. Almost complete inhibition of the enzyme that produces CE parallelled major increases in the amount of this lipid in VLDL particles. This indicates that the action of LCAT is not required for a reverse cholesterol transport. Cholesterol transport into VLDL may instead be governed by the charge and structural characteristics of plasma lipoproteins, which may regulate interfacial interactions with specific receptors and cholesterol storage depots on cell surfaces. Cell culture experiments indeed show that PI enhances cholesterol uptake from PI enriched plasma. In transformed hepatocytes (HEPG2 cells), PI-enrichment of plasma or HDL stimulates cellular cholesterol uptake, while PI enrichment of LDL does not. Without wishing to be limited by theory, it is considered that the enhanced uptake of cholesterol from PI-enriched HDL is not facilitated by a scavenger receptor-BI mediated pathway but is associated with a novel protein kinase C dependent uptake pathway. Therefore, it is considered that control of lipoprotein charge by the administration of charged compounds will allow for the manipulation of FC and CE influx/efflux from cell surfaces and the selective control of plasma cholesterol metabolism.

According to the invention, it is considered that this charge dependent control of cholesterol transport can be utilized to reduce the cholesterol in the blood stream and treat patients with high cholesterol levels (hypercholesterolemia) by using a negatively charged phospholipid. To evaluate this potential, the cholesterol lowering potential of PI was tested in Example 8 in the cholesterol-fed rabbit model, which is also a well-accepted model of atherosclerosis. It was shown that treating the animals for only seven days promotes major reductions in plasma cholesterol levels by selectively removing cholesterol from the LDL and VLDL particles (FIG. 8), and not from the HDL particles. The results were highly significant and greater in magnitude to that observed in earlier studies with simvastatin or a CETP inhibitor, that were administered to cholesterol-fed rabbits for a 3 month period (Okamoto et al.) The study of Okamoto et al. showed that cholesterol reducing treatments over a longer term (6 months) significantly reduced the development of atherosclerotic plaque in the aorta of the treated rabbits. Inasmuch as the current invention has much more marked short-term effects than the compositions used by Okamoto, it is anticipated that long term treatment of hypercholesterolemic rabbits or humans with negatively charged phospholipids will prevent the formation of atherosclerotic plaque in susceptible arteries.

The presence of a positively charged phospholipid, on the other hand, slows uptake of lipoprotein constituents. This can be used in the short term to slow uptake when needed, as for example when it is desired to keep a drug associated with a lipoprotein in the bloodstream for a longer than normal period.

Thus, according to the present invention there is provided a pharmaceutical composition comprising a synthetic or naturally occurring charged phospholipid. The pharmaceutical composition containing a negatively charged phospholipid is useful for lowering the level of cholesterol within a subject when administered in a suitable dosage form comprising anionic phospholipid as described herein. As outlined above, the administration of a negatively charged phospholipid is associated with sterol mobilization into bile and its excretion in faeces.

The present invention has been described with regard to preferred embodiments. However, it will be obvious to persons skilled in the art that a number of variations and modifications can be made without departing from the scope of the invention as described herein.

REFERENCES

Davidson, W. S., D. L. Sparks, S. Lund-Katz, and M. C. Phillips. 1994. The molecular basis for the difference in charge between pre-beta- and alpha-migrating high density lipoproteins. *J. Biol. Chem.* 269: 8959-8965.

Dobiasova, M., J. Stribrna, D. L. Sparks, P. H. Pritchard, and J. J. Frohlich. 1991. Cholesterol esterification rates in very low density lipoprotein- and low density lipoprotein-depleted plasma. Relation to high density lipoprotein subspecies, sex, hyperlipidemia, and coronary artery disease. *Artelioscler Thromb.* 11: 64-70.

Eisenberg, S., 1984. J. Lipid Res. 36:211-228.

Glomset, J. A. 1968. The plasma lecithins:cholesterol acyltransferase reaction. *Journal of Lipid Research.* 9: 155-167.

Guerin, M., P. J. Dolphin, and M. J. Chapman. 1994. A new in vitro method for the simultaneous evaluation of cholesteryl ester exchange and mass transfer between HDL and apoB-containing lipoprotein subspecies. Identification of preferential cholesteryl ester acceptors in human plasma. *Arterioscler Thromb.* 14: 199-206.

Jonas, A. 1987. Lecithin Cholesterol Acyltransferase. in *Plasma Lipoproteins* (Gotto A. M. Jr., ed.) Elsevier, Amsterdam, pp. 299-333.

Lagrost, L. 1997. The role of cholesteryl ester transfer protein and phospholipid transfer protein in the remodeling of plasma high-density lipoproteins. *Trends in Cardiovascular Medicine.* 7: 218-224.

Markwell, M. A., S. M. Haas, L. L. Bieber, and N. E. Tolbert. 1978. A modification of the Lowry procedure to simplify protein determination in membrane and lipoprotein samples. *Analytical Biochemistry.* 87: 206-210.

Miller, N. E., Thelle, D. S., Forde, O. H., and Mjos, O. D. 1977. The Tromso heart-study. High density Lipoprotein and Coronary Heart Disease: a prospective case-control study. Lancet 1: 965-968.

Okamoto, H., Yonemori F., Wakitani K., Minowa T, Maeda K, and Shinka H. 2000. A cholesteryl ester transfer protein inhibitor attenuates atherosclerosis in rabbits. Nature 406; 203-207

Phillips, M. C., K. L. Gillofte, M. P. Haynes, W. J. Johnson, S. Lund-Katz, and G. H. Rothblat. 1998. Mechanisms of high density lipoprotein-mediated efflux of cholesterol from cell plasma membranes. *Atherosclerosis.* 137: S13-S17.

Rigotti, K. T. Landschulz, S. Xu, H. H. Hobbs, and M. Krieger. 1996. Identification of scavenger receptor SR-BI as a high density lipoprotein receptor [see comments]. *Science*. 271: 518-520.

Schwartz, C. C., Halloran, L. G., Iahcevic, Z. R., Gregory, D. H., and Swell, L 1978. Science 200:62-64

Schaefer, E. J., Lichtenstein, A. H., Lamon-Fava, S., McNamara, J. R., and Ordovas, J. M. 1995. Lipoproteins, nutrition, aging, and atherosclerosis. *Am J. Clin. Nutr.* 61:726S-740S.

Sparks, D. L., and M. C. Phillips. 1992. Quantitative measurement of lipoprotein surface charge by agarose gel electrophoresis. *J Lipid Res*. 33: 123-130.

Tall, A. R. 1998. An overview of reverse cholesterol transport. *European Heart Journal*. 19 Suppl A: A31-A35.

The invention claimed is:

1. A method for treating dyslipidemia in a mammal in need thereof, the method consisting essentially of administering to the mammal in need thereof a therapeutically effective amount of a negatively charged phospholipid for achieving one or more of the following changes in serum lipid levels in said mammal: (1) an increase in the level of serum HDL-cholesterol; (2) a reduction in the level of serum VLDL-cholesterol and LDL-cholesterol; and (3) a reduction in the level of serum, triglycerides, wherein said negatively charged phospholipid is phosphatidylserine, phosphatidylglycerol, or phosphatidic acid, or a mixture thereof.

2. The method of claim 1, wherein the mammal is hyperlipidemic.

3. The method of claim 1, wherein the mammal is hypercholesterolemic.

4. The method of claim 1, wherein the mammal is hypertriglyceridemic.

5. The method of claim 1, wherein said negatively charged phospholipid is phosphatidylserine.

6. The method of claim 1, wherein said negatively charged phospholipid is phosphatidylglycerol.

7. The method of claim 1, wherein said negatively charged phospholipid is phosphatidic acid.

8. The method of claim 1, which increases the level of serum HDL-cholesterol in said mammal.

9. The method of claim 1, which reduces the level of serum VLDL-cholesterol or LDL-cholesterol or both in said mammal.

10. The method of claim 1, which reduces the level of serum cholesterol in said mammal.

11. The method of claim 1, which reduces the level of serum triglyceride in said mammal.

12. The method of claim 1, which enhances excretion of cholesterol in the faeces.

13. The method of claim 1, wherein the phospholipid is administered in a dose of 5 micromole to 100 micromole per kg body weight of the subject.

14. The method of claim 1, wherein the phospholipid is administered in a dose of 5 micromole to 20 micromole per kg body weight of the subject.

15. The method of claim 1, wherein the phospholipid is formulated as a food additive.

16. The method of claim 1, wherein the phospholipid is formulated as a medicament.

17. The method of claim 16, wherein the medicament is administered orally, intranasally, transdermally, or by injection.

18. The method of claim 1, wherein the phospholipid is in the form of unilamellar vesicles, multilamellar vesicles, multilamellar sheets, dispersion, micellar solutions, emulsions, or microemulsions.

19. The method of claim 1, wherein the phospholipid is in the form of a powder.

* * * * *

UNITED STATES PATENT AND TRADEMARK OFFICE
CERTIFICATE OF CORRECTION

| | | |
|---|---|---|
| PATENT NO. | : 7,390,783 B2 | Page 1 of 1 |
| APPLICATION NO. | : 10/956065 | |
| DATED | : June 24, 2008 | |
| INVENTOR(S) | : Daniel L. Sparks | |

It is certified that error appears in the above-identified patent and that said Letters Patent is hereby corrected as shown below:

Column 17, line 25, claim 1, delete "," after "level of serum"

Column 17, line 27, claim 1, "a mixture" should be -- any combination --

Signed and Sealed this

Seventh Day of October, 2008

JON W. DUDAS
*Director of the United States Patent and Trademark Office*